United States Patent [19]

Waddill et al.

[11] Patent Number: 4,581,421

[45] Date of Patent: Apr. 8, 1986

[54] EPOXY RESIN COMPOSITION CONTAINING A CURING AGENT WHICH IS A REACTION PRODUCT OF IMIDAZOLE AND AN ALDEHYDE

[75] Inventors: Harold G. Waddill; George P. Speranza, both of Austin, Tex.

[73] Assignee: Texaco, Inc., White Plains, N.Y.

[21] Appl. No.: 731,202

[22] Filed: May 6, 1985

[51] Int. Cl.$^4$ .......................................... C08G 59/64
[52] U.S. Cl. .................................. 525/504; 525/510; 528/107; 528/117; 528/246; 528/250
[58] Field of Search ................ 525/510, 504; 528/107, 528/246, 250, 117

[56] References Cited

U.S. PATENT DOCUMENTS

| | | |
|---|---|---|
| 3,324,050 | 6/1967 | Joo et al. ........................ 528/117 X |
| 3,493,630 | 2/1970 | Salensky ........................ 528/107 X |
| 3,697,462 | 10/1972 | Hoff .............................. 525/510 X |
| 3,963,667 | 6/1976 | Schreiber et al. |
| 4,206,104 | 6/1980 | Dowbenko et al. |
| 4,221,891 | 9/1980 | Erikson et al. |
| 4,490,510 | 12/1984 | Cummings ........................ 525/490 |
| 4,528,308 | 7/1985 | Waddill ........................ 528/111 X |

FOREIGN PATENT DOCUMENTS

EP126531 5/1984 European Pat. Off.

OTHER PUBLICATIONS

Alley, Peggy W., "The Imidazole-Formaldehyde Reaction Formation of 1-Imidazolemethanol," J. Org. Chem., vol. 40, No. 12 (1975).

"Epoxy Resin Technology, Developments Since 1979", Chemical Technology Review No. 24, pp. 81–83.

*Primary Examiner*—Earl Nielsen
*Attorney, Agent, or Firm*—Jack H. Park; Kenneth R. Priem

[57] ABSTRACT

The reaction product of imidazole and/or its alkyl derivatives and an aldehyde is described. Epoxy resins containing the product are useful in applications such as decorative coatings, encapsulations, adhesives, laminates, potting compounds, etc.

4 Claims, No Drawings

EPOXY RESIN COMPOSITION CONTAINING A CURING AGENT WHICH IS A REACTION PRODUCT OF IMIDAZOLE AND AN ALDEHYDE

BACKGROUND OF THE INVENTION

1. Field of the Invention

This invention relates to curable epoxy resins, and more particularly to epoxy resins cured with a reaction product of imidazole and an aldehyde.

2. Related Publications

Imidazole and imidazole derivatives are commonly used epoxy curing agents. However, imidazole is a solid material and, therefore, difficult to use conveniently when curing liquid epoxy systems.

Japanese Pat. No. J59190972-A, which is equivalent to EP No. 126531-A, discloses the reaction products of 2-ethyl-4-methyl imidazole and formaldehyde to form bis-imidazole products for use as epoxy curing agents.

In the present invention it has been discovered that a reaction product of solid imidazole or 2-methyl imidazole with an aldehyde in equal or greater molar quantity is, in most cases, a liquid which is easily dispersed uniformly into epoxy resins thereby providing a new and useful epoxy resin curing agent.

SUMMARY OF THE INVENTION

The invention is an epoxy resin composition comprising a vicinal polyepoxide having an epoxide equivalency of greater than about 1.8 and a curing amount of the reaction product of imidazole and/or 2-methyl imidazole and an aldehyde.

DESCRIPTION OF THE PREFERRED EMBODIMENTS

According to the instant inventive concept, a new epoxy resin curing composition is provided which is the reaction product of imidazole and/or its alkyl derivative, 2-methyl imidazole, and an aldehyde. This reaction product is mixed in a curing amount with a vicinal polyepoxide having an epoxide equivalency of greater than about 1.8 to provide a cured epoxy material.

Imidazole and/or its alkyl derivative, 2-methyl imidazole, are reacted with an aldehyde, especially formaldehyde, to form the epoxy curing agent of this invention. The preferred reactants are imidazole and formaldehyde.

Formaldehyde may be employed in any of its conventional forms such as, for example, an aqueous solution of formaldehyde called "formalin". Also, it may be used in "inhibited" methanol solution, as paraformaldehyde or as trioxane.

The preferred molar ratio of formaldehyde to imidazole is about 1.0 to about 2 moles. The reaction takes place at a wide range of temperatures and pressures. For example 10° C. to 150° C. and 1 to 100 atmospheres. We believe that our products are liquids because a mixture of products are obtained. Each product in this mixture is an epoxy curing agent. For example, when one mole of formaldehyde is allowed to react with one mole of imidazole a number of products are obtained as shown below.

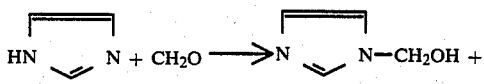

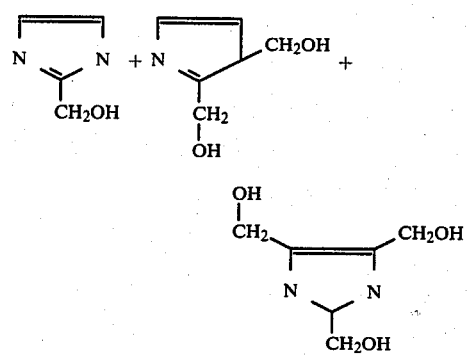

For a more detailed description of the imidazole.formaldehyde reaction the reader should refer to P. W. Alley, J. Org. Chem., Vol. 40, No. 12 (1975).

Generally, the amine cured vicinal polyepoxide containing compositions are organic materials having an average of at least 1.8 reactive 1,2-epoxy groups per molecule. These polyepoxide materials can be monomeric or polymeric, saturated or unsaturated, aliphatic, cycloaliphatic, aromatic or heterocyclic, and may be substituted if desired with other substituents besides the epoxy groups; e.g., hydroxyl groups, ether radicals, aromatic halogen atoms and the like.

Peferred polyepoxides are those of glycidyl ethers prepared by epoxidizing the corresponding allyl ethers or reacting, by known procedures, a molar excess of epichlorohydrin and an aromatic polyhydroxy compound; i.e., isopropylidene bisphenol, novolak, resorcinol, etc. The epoxy derivatives of methylene or isopropylidene bisphenols are especially preferred.

A widely used class of polyepoxides which are useful according to the instant invention includes the resinous epoxy polyethers obtained by reacting an epihalohydrin, such as epichlorohydrin, and the like, with either a polyhydric phenol or a polyhydric alcohol. An illustration, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'dihydroxydiphenylmethylpropylmethane, 2,3'-dihydroxydiphenylethylphenylmethane, 4,4'-dihydroxydiphenylpropylphenylmethane, 4,4'-dihydroxydiphenylbutylphenylmethane, 2,2'-dihydroxydiphenylditolylmethane, 4,4'-dihydroxydiphenyltolylmethylmethane and the like. Other polyhydric phenols which may also be co-reacted with an epihalohydrin to provide these epoxy polyethers are such compounds as resorcinol, hydroquinone, substituted hydroquinones; e.g., methylhydroquinone, and the like.

Among the polyhydric alcohols which can be co-reacted with an epihalohydrin to provide these resinous epoxy polyethers are such compounds as ethylene glycol, propylene glycols, butylene glycols, pentane diols, bis(4-hydroxycyclohexyl)dimethylmethane, 1,4-dimethylolbenzene, glycerol, 1,2,6-hexanetriol, trimethylolpropane, manniatol, sorbitol, erythritol, pentaerythritol, their dimers, trimers and higher polymers; e.g., polyethylene glycols, polypropylene glycols, triglycerol, dipentaerythritol and the like, polyallyl alcohol, polyhydric thioethers, such as 2,2'-, 3,3'-tetrahydroxydipropylsulfide and the like, mercapto alcohols such as monothioglycerol, dithioglycerol, and the like, polyhydric alcohol partial esters, such as monostearin, pentaerythritol monoacetate, and the like, and halogenated polyhydric alcohols such as the monochlorohydrins of glycerol, sorbitol, pentaerythritol and the like.

Another class of polymeric polyepoxides which can be amine cured and are in accordance with the instant invention includes the epoxy novolak resins obtained by reacting, preferably in the presence of a basic catalyst; e.g., sodium or potassium hydroxide, an epihalohydrin, such as epichlorohydrin, with the resinous condensate of an aldehyde; e.g., formaldehyde, and either a monohydric phenol; e.g., phenol itself, or a polyhydric phenol. Further details concerning the nature and preparation of these epoxy novolak resins can be obtained in Lee, H. and Neville, K., *Handbook of Epoxy Resins*, McGraw-Hill Book Co., New York, 1967.

Other polyepoxides known to those skilled in the art may be useful in this invention.

Optionally, the epoxy resin formulations of the instant invention can include an "accelerator" to speed the amine cure of the epoxy resin, especially at ambient temperatures. In several applications, such acceleration is beneficial, especially when an epoxy resin is used as an adhesive in flammable environment, thus making elevated temperature cure inconvenient or even hazardous. Lee, H. and Neville, K., *Handbook of Epoxy Resins*, pp. 7–14 describes the use of certain amine-containing compounds as epoxy curing agent-accelerators.

Many accelerators are known in the art which can be utilized in accordance with the instant invention. Examples include salts of phenols, salicyclic acids, amine salts of fatty acids, such as those disclosed in U.S. Pat. No. 2,681,901, and tertiary amines such as those disclosed in U.S. Pat. No. 2,839,480. Preferred accelerators in accordance with the instant invention are disclosed in U.S. Pat. Nos. 3,875,072 and 4,195,153.

It will further be realized that various conveniently employed additives can be admixed with the polyepoxide containing composition of the instant invention prior to final cure. For example, in certain instances it may be desired to add minor amounts of other polyalkyleneamine co-catalysts as herein described, or hardeners along with various other accelerators and curing agent systems well known in the art.

Additionally, conventional pigments, dyes, fillers, flame retarding agents and the like which are compatible; natural or synthetic resins can be added.

Furthermore, although not preferred, known solvents for polyepoxide materials such as toluene, benzene, xylene, dioxane, ethylene glycol monomethyl ether and the like can be used. The polyepoxide resins containing the additives of the instant invention can be used in any of the above applications for which polyepoxides are customarily used. The compositions of the instant invention can be used as impregnants, surface coatings, encapsulating compositions, laminants and, particularly and most importantly, as adhesives for bonding metallic elements or structures permanently together.

The following examples illustrate the nature of the instant invention but are not intended to be limitative thereof.

EXAMPLE 1

To a 250 ml three-necked flask equipped with a stirrer, thermometer and condenser were added 34 g of imidazole (0.5 moles) and 41 g of 37% formalin. The reactants exothermed from 26° to 35° C. They were then heated to 90° C. and held for four hours at 90° C. The product was then held at 90° C. and 42 mm vacuum to remove the rest of the water. The NMR spectra indicated that most of the sample contained

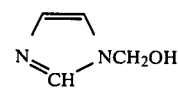

In a similar manner, formaldehyde was allowed to react with 2-methyl imidazole.

EXAMPLE 2

Imidazole or Imidazole.Formaldehyde Condensate Formulations With Epoxy Resin

| Component | Formulation | | | |
|---|---|---|---|---|
| | 1 | 2 | 3 | 4 |
| EPON ® 828 | 100 | 100 | 100 | 100 |
| Imidazole | 3 | — | — | — |
| Imidazole.CH$_2$O Condensate | — | 3 | — | — |
| 2-Methyl Imidazole | — | — | 3 | — |
| 2-Me Imidazole.CH$_2$O | — | — | — | 6 |

EXAMPLE 3

Curing Characteristics of Imidazole.Formaldehyde Condensates of Example 2

| Formulation | Onset Temperature, °C. | Peak Temperature, °C. | Tg, °C. |
|---|---|---|---|
| 1 | 115.6 | 126.9 | 166.4 |
| 2 | 117.2 | 132.7 | 166.6 |
| 3 | 111.7 | 121.8 | 169.8 |
| 4 | 115.0 | 125.0 | 165.0 |

EXAMPLE 4

Properties of an Epoxy Resin Cured With Imidazole Condensates of Example 2

| Properties of Cured ⅛ inch Castings[1] | Formulation | | | |
|---|---|---|---|---|
| | 1 | 2 | 3 | 4 |
| Izod impact strength, ft/lbs/in | 0.19 | 0.12 | 0.12 | 0.10 |
| Tensile strength, psi | 3000 | 6400 | 3100 | 2700 |
| Tensile modulus, psi | 417000 | 386000 | 367000 | 366000 |
| Elongation at break, % | 0.7 | 2.3 | 0.9 | 0.8 |
| Flexural strength, psi | 7500 | 10900 | 6000 | 5800 |
| Flexural modulus, psi | 401000 | 356000 | 369000 | 357000 |
| HDT, °C. 264 psi/66 psi | 122.5/139 | 145/158 | 155/165 | 159/170 |
| Shore D hardness, 0–10 sec | 82–80 | 82–78 | 80–79 | 83–82 |

[1]Cured 2 hours at 80° C., 3 hours at 150° C.

We claim:

1. An epoxy resin composition comprising
   a. a vicinal polyepoxide having an epoxide equivalency of greater than about 1.8, and
   b. a curing amount of the reaction product of formaldehyde and imidazole in a molar ratio of about 1.0 to 2.0.

2. An epoxy resin composition comprising
   a. a vicinal polyepoxide having an epoxide equivalency of greater than about 1.8, and
   b. a curing amount of the reaction product of formaldehyde and 2-methyl imidazole in a molar ratio of about 1.0 to 2.0.

3. In a method for curing a vicinal polyepoxide having an epoxide equivalency of greater than about 1.8 wherein an effective amount of a curing agent is intimately mixed with the vicinal polyepoxide under epoxy resin curing conditions, the improvement which comprises using, as the curing agent, the reaction product of formaldehyde and imidazole in a molar ratio of about 1.0 to 2.0.

4. In a method for curing a vicinal polyepoxide having an epoxide equivalency of greater than about 1.8 wherein an effective amount of a curing agent is intimately mixed with the vicinal polyepoxide under epoxy resin curing conditions, the improvement which comprises using, as the curing agent, the reaction product of formaldehyde and 2-methyl imidazole in a molar ratio of about 1.0 to 2.0.

* * * * *